United States Patent

Kirsch et al.

[11] Patent Number: 6,056,895
[45] Date of Patent: May 2, 2000

[54] FLUOROCYCLOHEXANE DERIVATIVES, AND LIQUID-CRYSTALLINE MEDIUM

[75] Inventors: Peer Kirsch, Darmstadt; Kazuaki Tarumi, Seeheim; Joachim Krause; Rolf Sander, both of Dieburg; Andreas Ruhl, Rossdorf, all of Germany

[73] Assignee: Merck Patent Gesellschaft mit Beschrankter Haftung, Germany

[21] Appl. No.: 09/055,891

[22] Filed: Apr. 7, 1998

[30] Foreign Application Priority Data

Apr. 7, 1997 [DE] Germany ............... 197 14 231

[51] Int. Cl.[7] ............... C09K 19/30; C07C 19/08
[52] U.S. Cl. ............... 252/299.63; 570/130
[58] Field of Search ............... 570/130; 252/299.63

[56] References Cited

U.S. PATENT DOCUMENTS

| | | | |
|---|---|---|---|
| 4,510,069 | 4/1985 | Eidenschink et al. | 252/299.61 |
| 4,985,583 | 1/1991 | Eidenschink et al. | 558/431 |
| 4,986,931 | 1/1991 | Eidenschink et al. | 252/299.63 |
| 5,108,562 | 4/1992 | Eidenschink et al. | 252/299.63 |

FOREIGN PATENT DOCUMENTS 2248059   3/1992   European Pat. Off. .

OTHER PUBLICATIONS

English Abstract of JP 5125002, 1998.
English Abstract of JP 5229979, 1998.

Primary Examiner—C. H. Kelly
Attorney, Agent, or Firm—Millen, White, Zelano & Branigan, P.C.

[57] ABSTRACT

The invention relates to fluorocyclohexane derivatives of the formula I

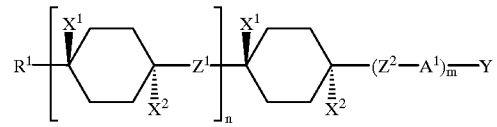

in which n, m, $R^1$, $X^1$, $X^2$, $Z^1$, $Z^2$, $A^1$ and Y are as defined above.

19 Claims, No Drawings

FLUOROCYCLOHEXANE DERIVATIVES, AND LIQUID-CRYSTALLINE MEDIUM

The invention relates to novel fluorocyclohexane derivatives of the formula I

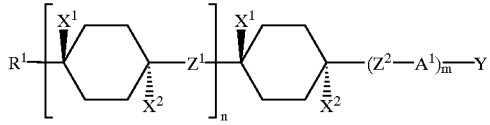

in which
Y is alkyl or alkoxy having 1 to 10 carbon atoms which is unsubstituted or at least monosubstituted by halogen, alkenyl or alkenyloxy having 2 to 10 carbon atoms which is unsubstituted or at least monosubstituted by —CN, —$CF_3$ or —F, or Y is —CN, —F, —$CF_3$, —$OCHF_2$, —$OCF_3$, —$OCHFCF_3$ or —$OCF_2CF_3$, $X^1$ and $X^2$ are each, independently of one another, H or F in the axial position, where $X^1$ and $X^2$ are not simultaneously H on each individual cyclohexane ring substituted by $X^1$ and $X^2$, $R^1$ is H, an alkyl or alkenyl radical having 1–12 or 2–12 carbon atoms respectively which is unsubstituted, monosubstituted by CN or $CF_3$ or at least monosubstituted by halogen, where one or more $CH_2$ groups in these radicals may also, in each case independently of one another, be replaced by —O—, —S—, —CO—,

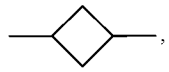

—CO—O—, —O—CO— or —O—CO—O—in such a way that the heteroatoms are not linked directly to one another, $A^1$ a) is a trans-1,4-cyclohexylene radical, in which, in addition, one or more non-adjacent $CH_2$ groups may be replaced by —O— and/or —S—,
  b) is a 1,4-phenylene radical, in which, in addition, one or two CH groups may be replaced by N,
  c) is a radical selected from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl,
  d) is 1,4-cyclohexenylene,
  where the radicals a), b) and d) may be substituted by CN, Cl or F, $Z^1$ and $Z^2$ are each, independently of one another, —CO—O—, —O—CO—, —$CH_2$O—, —O—, —O—$CH_2$—, —$CH_2CH_2$—, —CH=CH—, —C≡C— or a single bond, n is 1,2,3 or 4, and
m is 0, 1 or 2, where
m+n is 1,2,3 or 4.

In addition, the invention relates to the use of compounds of the formula I as components of liquid-crystalline media, and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases (DAP) or electrically controlled birefringence (ECB), or the effect of dynamic scattering. The substances employed hitherto for this purpose all have certain disadvantages, for example inadequate stability to exposure to heat, light or electric fields, or unfavorable elastic and/or dielectric properties.

Compounds containing fluorocyclohexane units are disclosed, for example, in JP 05125002, JP 05229979 and EP 0107759, but no compounds containing two or more fluorocyclohexane rings are described therein.

An object of the invention was finding novel, stable, liquid-crystalline or mesogenic compounds which are suitable as components of liquid-crystalline media, in particular for TFT and STN displays.

Upon further study of the specification and appended claims, further objects and advantages of this invention will become apparent to those skilled in the art.

It has now been found that the compounds of the formula I are eminently suitable as components of liquid-crystalline media. They can be used to obtain stable liquid-crystalline media, particularly suitable for TFT or STN displays. The novel compounds are distinguished, in particular, by high thermal stability, which is advantageous for a high holding ratio, and exhibit favorable clearing points at the same time as comparatively low rotational viscosity values. The compounds of the formula I have highly negative dielectric anisotropy and are therefore particularly suitable for displays based on the effect of deformation of aligned phases.

The provision of compounds of the formula I very generally considerably broadens the range of liquid-crystalline substances which are suitable from various applicational points of view for the preparation of liquid-crystalline mixtures.

The compounds of the formula I have a broad range of applications. Depending on the choice of substituents, these compounds can be used as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I, and to liquid-crystal display elements, in particular electro-optical display elements, which contain media of this type.

Above and below, n, m, $R^1$, $X^1$, $X^2$, $Z^1$, $Z^2$, $A^1$ and Y are as defined above, unless expressly stated otherwise.

For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bco denotes a bicyclo[2.2.2]octylene radical, where Cyc and/or Phe may be unsubstituted or monosubstituted or polysubstituted by Cl, F or CN.

W denotes the following structural unit:

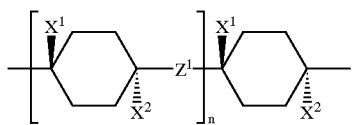

in which $X^1$, $X^2$, $Z^1$ and n are as defined above.

The formula I covers as preferred compounds those of the subformula Ia:

$R^1$—W—Y      Ia

Compounds of the subformulae Ib and Ic:

$R^1$—W—$A^1$—Y      Ib

R—W—$Z^2$—$A^1$—Y      Ic

Compounds of the subformulae Id to Ig:

$R^1$—W—$A^1$—$A^1$—Y      Id $R^1$—W—$A^1$—$Z^2$—$A^1$—Y      Ie $R^1$—W—$Z^2$—$A^1$—$A^1$—Y      If $R^1$—W—$Z^2$—$A^1$—$Z^2$—$A^1$—Y      Ig and compounds of the subformulae Ih to Io:

$R^1$—W—$A^1$—$A^1$—$A^1$—Y      Ih $R^1$—W—$Z^2$—$A^1$—$A^1$—$A^1$—Y      Ii $R^1$—W—$A^1$—$Z^2$—$A^1$—$A^1$—Y      Ij $R^1$—W—$A^1$—$A^1$—$Z^2$—$A^1$—Y      Ik $R^1$—W—$Z^2$—$A^1$—$Z^2$—$A^1$—$A^1$—Y      Il $R^1$—W—$Z^2$—$A^1$—$A^1$—$Z^2$—$A^1$—Y      Im $R^1$—W—$A^1$—$Z^2$—$A^1$—$Z^2$—$A^1$—Y      In $R^1$—W—$Z^2$—$A^1$—$Z^2$—$A^1$—$Z^2$—$A^1$—Y      Io

Of these, particular preference is given to those of the subformulae Ia, Ib, Id, Ie, If, Ih, Ii and Ij.

The preferred compounds of the subformula Ib include those of the subformulae Iba and Ibb:

$R^1$—W—Phe—Y      Iba $R^1$—W—Cyc—Y      Ibb

The preferred compounds of the subformula Ic include those of the subformulae Ica and Icb:

$R^1$—W—$Z^2$—Phe—Y      Ica $R^1$—W—$Z^2$—Cyc—Y      Icb

The preferred compounds of the subformula Id include those of the subformulae Ida to Idg:

$R^1$—W—Cyc—Cyc—Y      Ida $R^1$—W—Cyc—Phe—Y      Idb $R^1$—W—Phe—Phe—Y      Idc $R^1$—W—Pyd—Phe—Y      Idd $R^1$—W—Phe—Cyc—Y      Ide $R^1$—W—Dio—Phe—Y      Idf $R^1$—W—Pyr—Phe—Y      Idg

Of these, those of the formulae Ida, Idb, Idc and Ide are particularly preferred.

Preferred compounds of the subformula Ie include those of the subformulae Iea to Ieg:

$R^1$—W—Cyc—$Z^2$—Cyc—Y      Iea $R^1$—W—Cyc—$Z^2$—Phe—Y      Ieb $R^1$—W—Phe—$Z^2$—Phe—Y      Iec $R^1$—W—Pyr—$Z^2$—Phe—Y      Ied $R^1$—W—Pyd—$Z^2$—Phe—Y      Iee $R^1$—W—Cyc—CH$_2$—CH$_2$—Phe—Y      Ief $R^1$—W—$A^1$—CH$_2$CH$_2$—Phe—Y      Ieg.

The preferred compounds of the subformula If include those of the subformulae Ifa to Ifh:

$R^1$—W—$Z^2$—Cyc—Cyc—Y      Ifa $R^1$—W—CH$_2$CH$_2$—$A^1$—$A^1$—Y      Ifb $R^1$—W—$Z^2$—Cyc—Phe—Y      Ifc $R^1$—W—OCO—$A^1$—Phe—Y      Ifd $R^1$—W—$Z^2$—Phe—Phe—Y      Ife $R^1$—W—$Z^2$—Pyr—$A^1$—Y      Iff $R^1$—W—$Z^2$—Pyd—$A^1$—Y      Ifg $R^1$—W—$Z^2$—Dio—$A^1$—Y      Ifh.

Of these, those of the subformulae Ifa, Ifb, Ifc and Ife are particularly preferred.

Preferred compounds of the subformula Ig include those of the subformulae Iga to Ige:

$R^1$—W—CH$_2$CH$_2$—Phe—$Z^2$—$A^1$—Y      Iga $R^1$—W—COO—$A^1$—$Z^2$—Phe—Y      Igb $R^1$—W—$Z^2$—Cyc—$Z^2$—Cyc—Y      Igc $R^1$—W—$Z^2$—Phe—$Z^2$—Phe—Y      Igd $R^1$—W—CH$_2$CH$_2$—Cyc—$Z^2$—Phe—Y      Ige.

The preferred compounds of the subformulae Ih to Io include those of the subformulae Ip to Iw:

$R^1$—W—$A^1$—Cyc—Cyc—Y      Ip $R^1$—W—$A^1$—Cyc—Phe—Y      Iq $R^1$—W—$A^1$—CH$_2$CH$_2$—$A^1$—Phe—Y      Ir $R^1$—W—$Z^2$—Cyc—$Z^2$—$A^1$—Phe—Y      Is $R^1$—W—Phe—Phe—Phe—Y      It $R^1$—W—Phe—$Z^2$—$A^1$—Phe—Y      Iu $R^1$—W—$A^1$—Phe—$Z^2$—Phe—Y      Iv $R^1$—W—$Z^2$—$A^1$—Cyc—$Z^2$—Phe—Y      Iw.

A group of preferred compounds of the formula I includes the compounds of the subformulae Ia1, Ib1, Ib2 and Ie1:

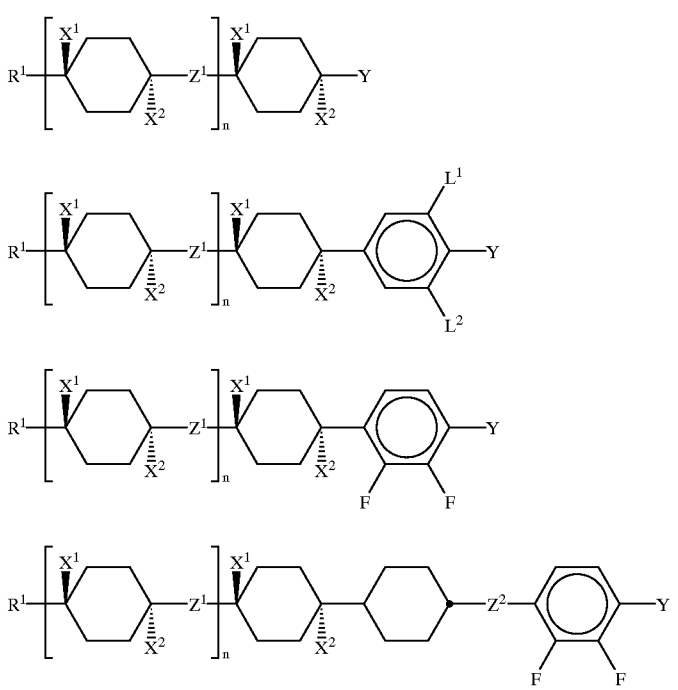

Ia1

Ib1

Ib2

Ie1 in which $R^1$, $X^1$, $X^2$, $Z^1$, $Z^2$, n and Y are as defined above, and $L^1$, $L^2$ and $L^4$, independently of one another, are F or H.

Y is preferably —CN, —F, —$CF_3$, —$OCF_3$ or straight-chained alkyl having 1 to 10 carbon atoms or alkenyl having 2 to 10 carbon atoms. The preferred meaning of n is 1 or 2. When substituted, the maximum number of substituents on the Y group is preferably 5 or less; or, in the case of fluorine substituents, the maximum is perfluoro substitution. Compounds of the formula I in which $X^1$ and $X^2$ are not simultaneously F on each individual cyclohexane ring substituted by $X^1$ and $X^2$ are preferred.

In the compounds of the formulae above and below, $R^1$ is preferably straight-chain alkyl having 1 to 10 carbon atoms or alkenyl having 2 to 10 carbon atoms, furthermore preferably alkoxy having 1 to 10 carbon atoms. When halogen substituted, the maximum number of substituents on the $R^1$ group is the number for perhalo substitution.

$A^1$ is preferably Phe, Cyc, Che, Pyd, Pyr or Dio. The compounds of the formula I preferably contain not more than one of the radicals Bco, Pyd, Pyr, Dio and Dit.

If more than one ring $A^1$ is present, the two rings can have identical or different meanings. The same also applies to the bridges $Z^1$ and $Z^2$, and to $X^1$ and $X^2$.

Preference is also given to compounds of the formula I and all subformulae in which $A^1$ is 1,4-phenylene which is monosubstituted or disubstituted by F or CN.

$A^1$ is preferably

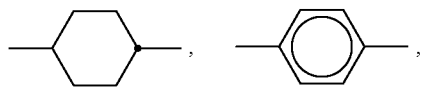

-continued

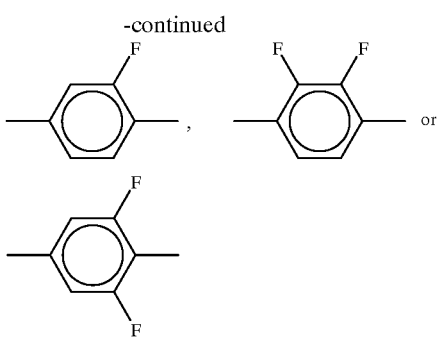

m is preferably 0 or 1, particularly preferably 0. $Z^1$ and $Z^2$, independently of one another, are preferably —$CH_2CH_2$—, —CH=CH— or a single bond, particularly preferably a single bond.

Preference is given to compounds of the formula I in which $R^1$ and Y are simultaneously alkyl having 1 to 10 carbon atoms, while m is 0.

Particular preference is furthermore given to compounds of the formula I which are characterized in that $R^1$ is straight-chain alkyl or alkoxy having 1 to 10 carbon atoms or alkenyl having 2 to 10 carbon atoms, and Y is alkyl having 1 to 10 carbon atoms, alkenyl having 2 to 10 carbon atoms, —CN, —F, —$CHF_2$ or —$OCF_3$.

The 1,4-cyclohexenylene group preferably has the following structures:

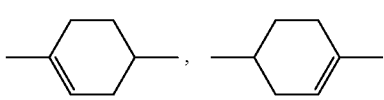

The following group of compounds of the subformulae I1 to I16 represents a further preferred embodiment of the invention:

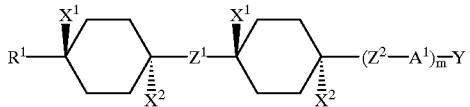
I1
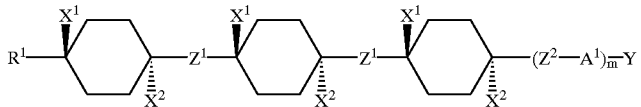
I2
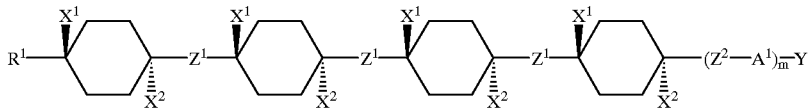
I3
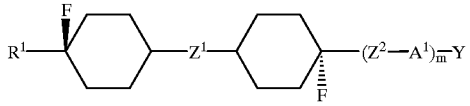
I4
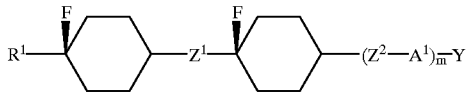
I5
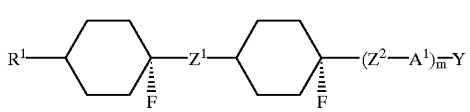
I6
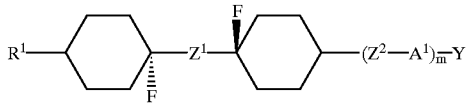
I7
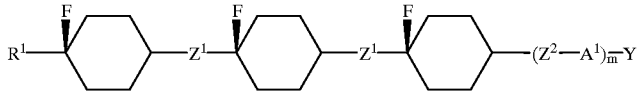
I8
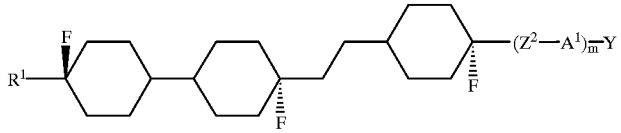
I9
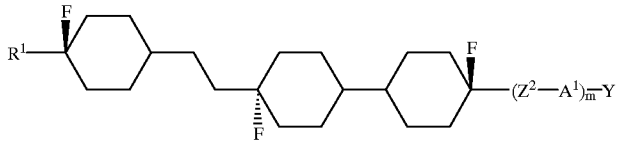
I10
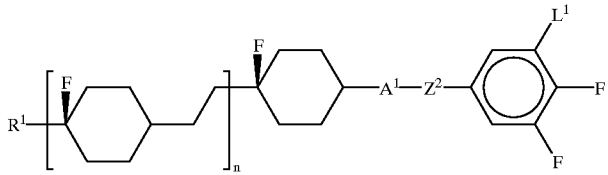
I11

-continued
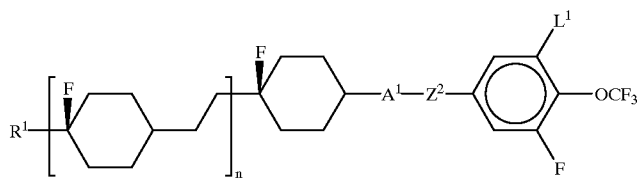
I12
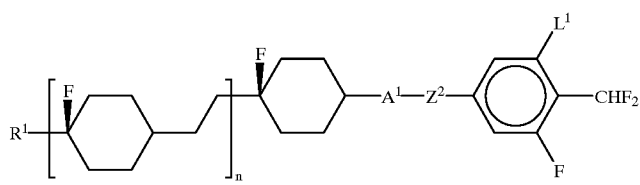
I13
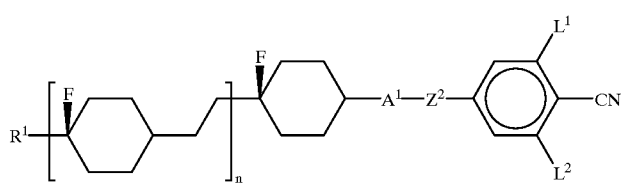
I14
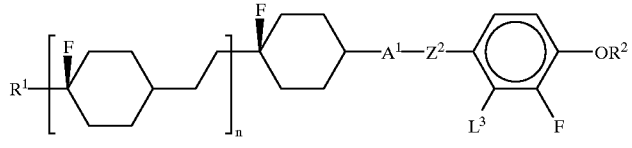
I15
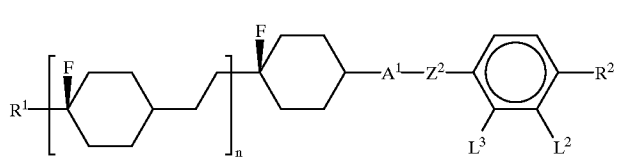
I16
in which $R^1$, $X^1$, $X^2$, $Z^1$, $Z^2$, $A^1$, n, m and Y are as defined above, $L^1$, $L^2$, and $L^3$ are each, independently of one another, F or H, and $R^2$ is alkyl having 1 to 10 carbon atoms or alkenyl having 2 to 10 carbon atoms.
Particular preference is furthermore given to the compounds of the formulae I1a to I8a in the following group:
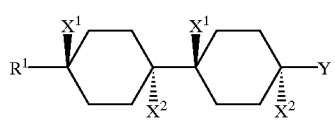
I1a
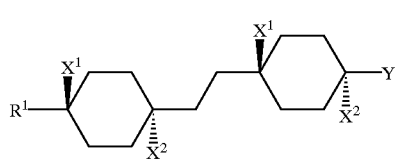
I1b
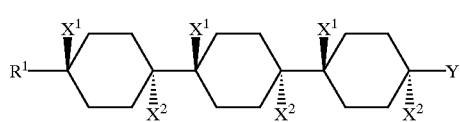
I2a
-continued
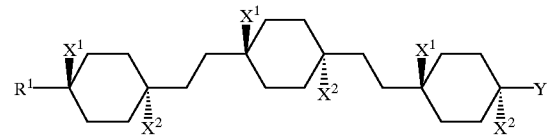
I2b
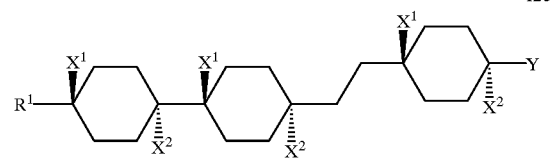
I2c
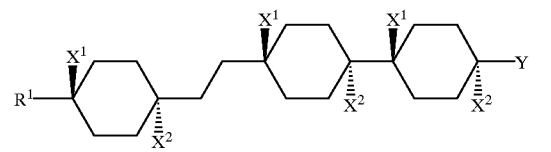
I2d
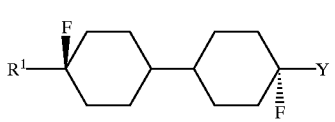
I4a

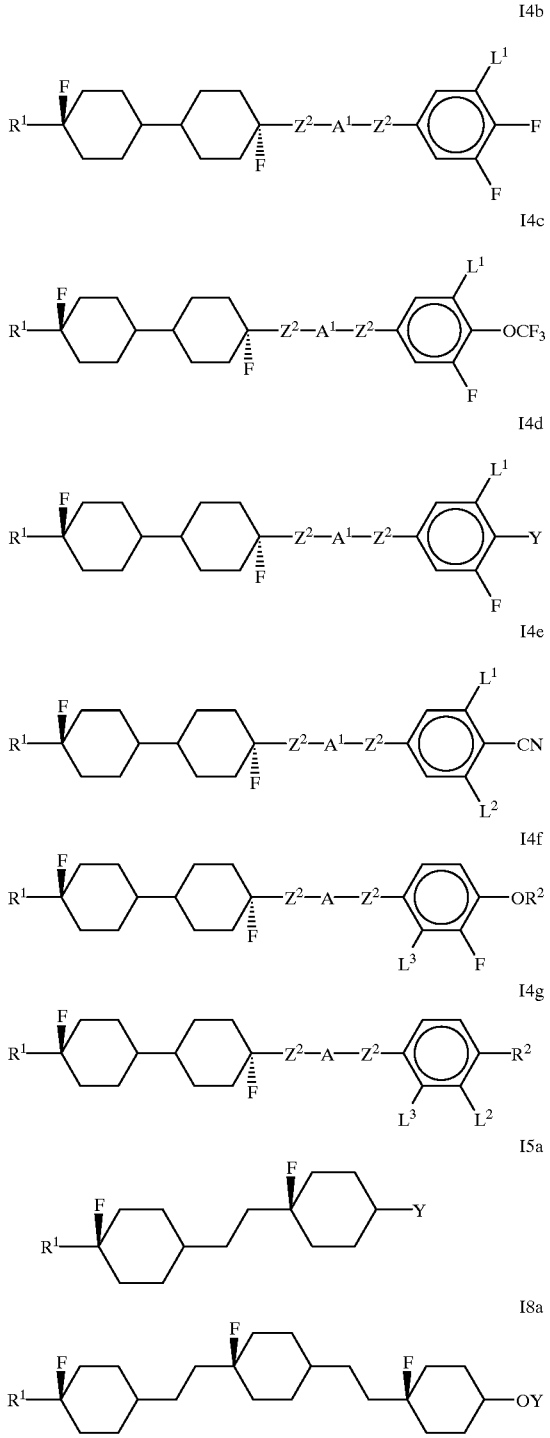

in which $R^1$, $X^1$, $X^2$, $Z^1$, $Z^2$, $A^1$ n, m and Y are as defined above, $L^1$, $L^2$ and $L^3$ are each, independently of one another, F or H and R 2 is alkyl having 1 to 10 carbon atoms or alkenyl having 2 to 10 carbon atoms.

In all the compounds of the formula I, the fluorine atom in the fluorocyclohexane units is in the axial position, while the other substituents are in the trans-arrangement with respect to one another. This correlation is illustrated by the example with reference to the compounds of the formulae I4a and I5a:

in which $R^1$ and Y are as defined above.

If $R^1$ in the formulae above and below is an alkyl radical and/or alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxa-nonyl, or 2-, 3-, 4-, 5-, 6-, 7-, 8- or 9-oxadecyl.

If $R^1$ is an alkyl radical in which one $CH_2$ group has been replaced by —CH=CH—, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-l-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ is an alkyl radical in which one $CH_2$ group has been replaced by —O— and one has been replaced by —CO—, these are preferably adjacent. These thus contain one acyloxy group —CO—O— or one oxycarbonyl group —O—CO—. These are preferably straight-chain and have 2 to 6 carbon atoms. Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ is an alkyl radical in which one $CH_2$ group has been replaced by unsubstituted or substituted —CH=CH— and an adjacent $CH_2$ group has been replaced by CO or CO—O or O—CO—, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl and 9-methacryloyloxynonyl. If $R^1$ is an alkyl or alkenyl radical which is monosubstituted by CN or $CF_3$, this radical is preferably straight-chain, and the substitution by CN or $CF_3$ is in the ω-position.

If $R^1$ is an alkyl or alkenyl radical which is at least monosubstituted by halogen, this radical is preferably straight-chain, and halogen is preferably F or Cl. In the case of multiple substitution, halogen is preferably F. The resulting radicals also include perfluorinated radicals. In the case of monosubstitution, the fluorine or chlorine substituent can be in any desired position, but is preferably in the Ω-position.

Compounds of the formula I containing branched wing groups $R^1$ may occasionally be of importance due to better solubility in the customary liquid-crystalline base materials, but in particular as chiral dopes if they are optically active. Smectic compounds of this type are suitable as components for ferroelectric materials.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The formula I covers the racemates of these compounds and the optical antipodes, and mixtures thereof.

Of these compounds of the formula I and the subformulae, preference is given to those in which at least one of the radicals present therein has one of the preferred meanings indicated.

In the compounds of the formula I, preference is given to the stereoisomers in which the rings Cyc and piperidine are trans-1,4-disubstituted. Those of the abovementioned formulae which contain one or more groups Pyd, Pyr and/or Dio in each case include the two 2,5-positional isomers.

Some very particularly preferred subgeneric groups of compounds of the formula I are those of the subformulae I17 to I42:

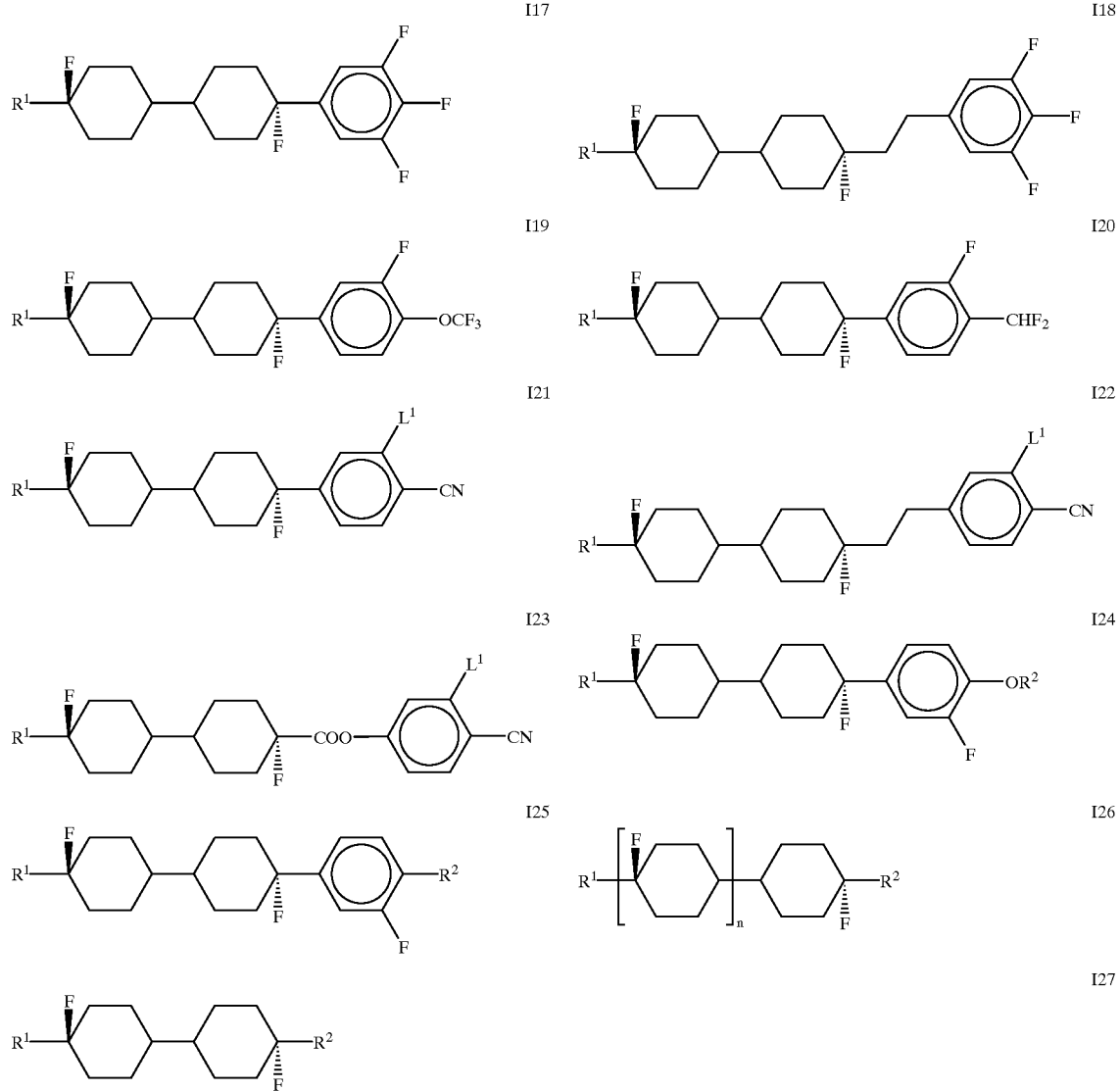

-continued
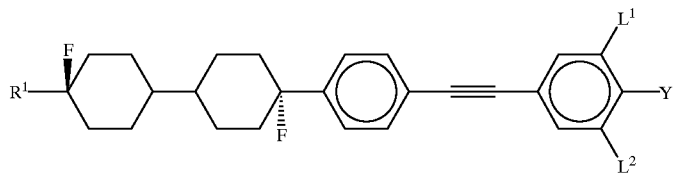
I28
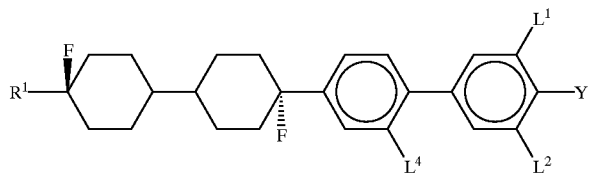
I29
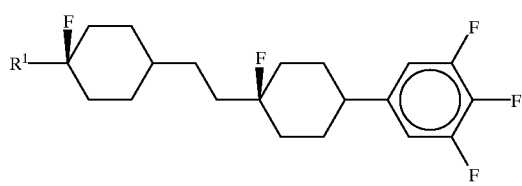
I30
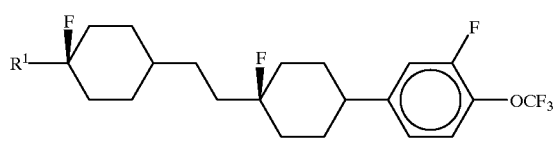
I31
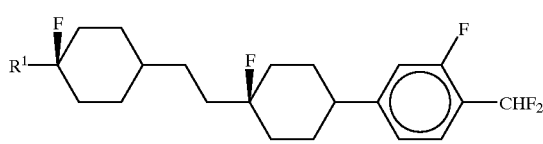
I32
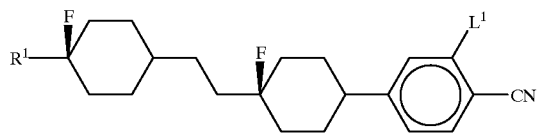
I33
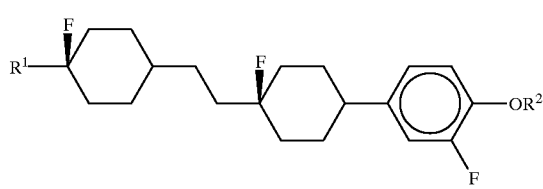
I34
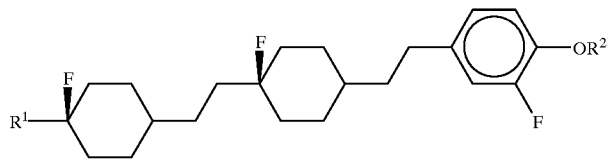
I35
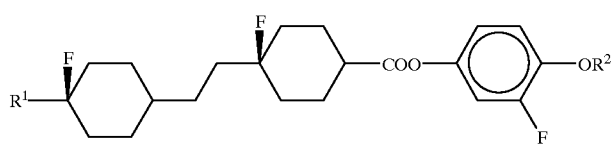
I36
I37
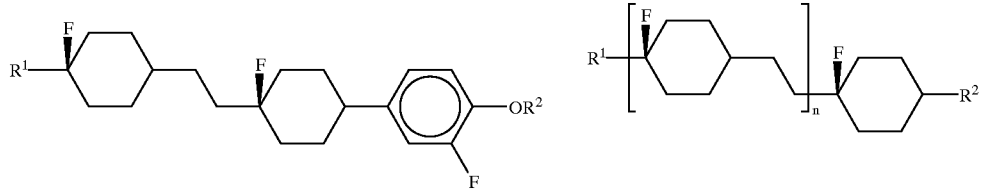
I38

I39

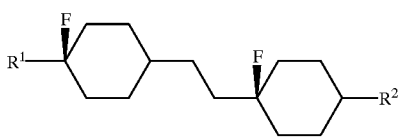

I40

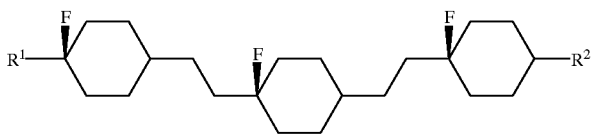

I41

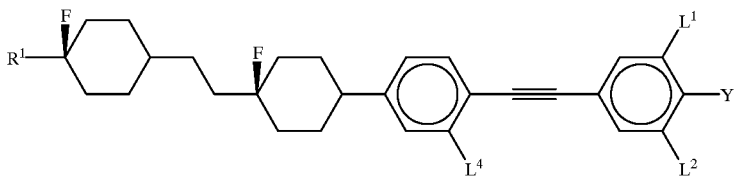

I42

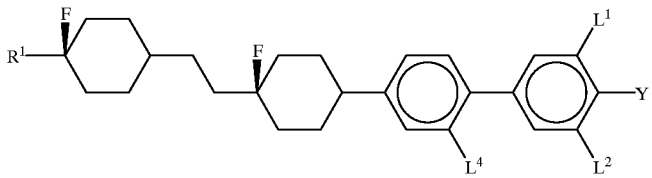

in which $R^1$, $R^2$, $L^1$, $L^2$, $L^4$, n and Y are as defined above.

Very particularly preferred compounds from this group are those of the formulae I17, I26, I27, I30, I38 and I39.

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions.

Use can also be made here of variants which are known per se, but are not described here in greater detail.

The novel axially fluorinated compounds of the formula I can be synthesized by a general process, which is included in the subject matter of the present invention.

In this process for the preparation of axially fluorinated cyclohexanes of the formula II

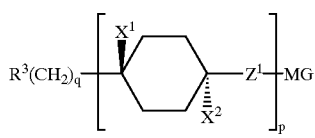
II hydrogen fluoride is adducted onto unsaturated starting compounds of the formula III $R^3(CH_2)_q$—$(B)_p$—MG    III in which B is

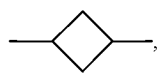

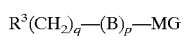

$R^3$ is H, an alkyl or alkenyl radical having 1–12 carbon atoms which is unsubstituted, monosubstituted by CN or $CF_3$ or at least monosubstituted by halogen, where one or more $CH_2$ groups in these radicals may also, in each case independently of one another, be replaced by —O—, —S—, —CO—, —CO—O—, —O—CO or —O—CO—O—in such a way that heteroatoms are not linked directly to one another,
p is 1, 2, 3, 4 or 5,
q is 0 or 1,
and $X^1$, $X^2$ and $Z^1$ are as defined above, while MG is a mesogenic group, where no or only small amounts of equatorially fluorinated compounds are formed, and, in the case of multiple fluorination, no intramolecular reactions take place.

The term "mesogenic group" is known to the person skilled in the art (for example H. Kelker, H. Hatz, Handbook of Liquid Crystals) and represents a rod-like radical consisting of ring members, optionally bridging members and wing groups.

If B occurs more than once, it can in each case have the same or different meanings.

MG is preferably the following radical:

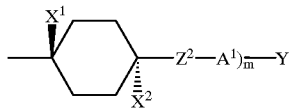

in which $X^1$, $X^2$, $A^1$, $Z^2$, m and Y are as defined above. p is preferably 1, 2 or 3, and q is preferably 0.

The preparation of fluorocyclohexanes from the corresponding cyclohexanes by reaction with molecular fluorine is known (for example S. Rozen, C. Gal, J. Org. Chem. 52 (1987) 2769), but this reaction only gives low yields. Furthermore, the extreme reactivity of the fluorine results, in the case of functionalized starting compounds, in undesired side reactions and makes transfer to a larger scale extremely complex technically. The use of DAST (diethylaminosulphur trifluoride) for tertiary cyclohexanols, which is described in various publications for the preparation of fluorocyclohexanes (for example JP 05125002, JP 05229979), is not feasible on an industrial scale owing to the toxicity, explosivity and high price of DAST. Finally, fluorocyclohexanes can be obtained by adduction of hydrogen fluoride onto corresponding unsaturated starting compounds. This can be achieved by using hydrogen fluoride under pressure or by means of amine/hydrogen fluoride adducts (for example A. V. Grosse, C. B. Linn, J. Org. Chem. 3, (1938) 26; G. A. Olah, M. Nojima, I. Kerekes, Synthesis, (1973), 779; G. A. Olah, X-Y. Li, Q. Wang, G. K. S. Prakash, Synthesis (1993) 693).

In general, however, the adduction of hydrogen fluoride onto starting compounds containing appropriately substituted double bonds does not give rise to expectations of a uniform configuration of the products, i.e. it is stated that both axially and equatorially fluorinated products are formed in the preparation of compounds of the formula I, so that the yield of the desired axially fluorinated product is very low. This effect is particularly disadvantageous in the case of polyfluorinations. It is known that compounds containing more than one double bond tend to form intramolecular carbon—carbon bonds on acidic catalysis. For polyfluorinations of starting compounds containing more than one double bond, it must therefore be expected that adduction of hydrogen fluoride would result in the formation of additional undesired by-products, which reduce the yield of axially fluorinated compounds.

None of the publications indicates how the axially fluorinated cyclohexanes of the formula II can be prepared without having to accept the above disadvantages. A further object of the invention was therefore to provide a process for the preparation of axially fluorinated compounds of the formula II in which no or only small amounts of equatorially fluorinated compounds are produced, and, in the case of multiple fluorination, no intramolecular reactions occur. The preparation should be possible without risk, should be economical and should be environmentally compatible on a large industrial scale.

It has been found that no or only small amounts of equatorially fluorinated compounds are produced and, in the case of multiple fluorination, no intramolecular reactions occur if axially fluorinated cyclohexanes of the formula II are prepared by adducting hydrogen fluoride onto corresponding unsaturated starting compounds of the formula III.

The process is simple to carry out, starting compounds of the formula III being reacted either as pure substances or in suitable solvents at temperatures of from −78° C. to +50° C., preferably at −30° C. to +40° C.

It is possible to start from mixtures of the compounds of the formula III which differ in the position of the double bonds.

Preferred solvents are halogenated hydrocarbons or ethers, particularly preferably dichloromethane, trichloromethane, trichloroethane, diethyl ether or tetrahydrofuran.

Hydrogen fluoride can be employed either without further additives at low temperatures and/or under pressure or alternatively in the form of amine adducts. Preferred amine adducts are those of pyridine, polyvinyl pyridine and trialkylamines, such as triethylamine or tributylamine. Particular preference is given to solutions of hydrogen fluoride in pyridine, the proportion by weight of the hydrogen fluoride preferably being 70%, based on the solution.

Preference is given to an embodiment of the novel process in which the alkene and the hydrogen fluoride are in a molar ratio of between 1.0 and 10.

The starting materials for the preparation of the compounds of the formula I can, if desired, also be formed in situ by not isolating them from the reaction mixture, but instead immediately converting them further into the compounds of the formula I.

The novel compounds can be prepared, for example, in accordance with the following reaction schemes:

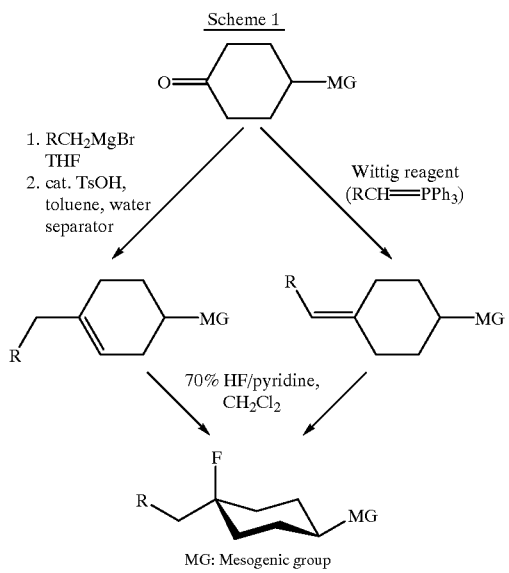

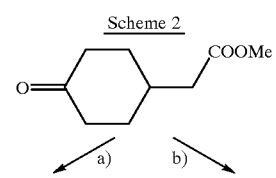

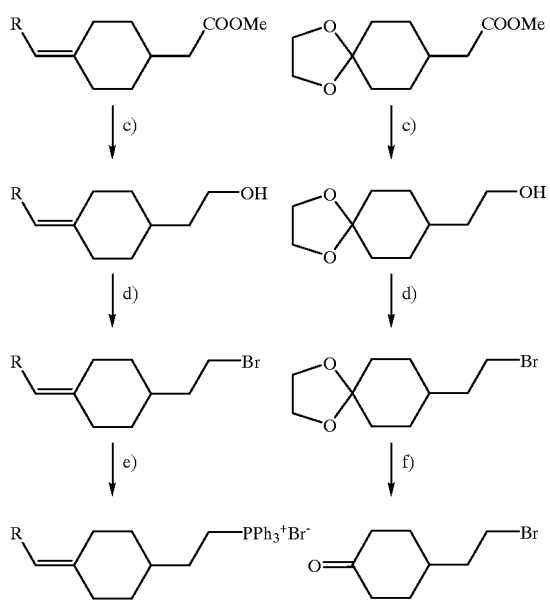
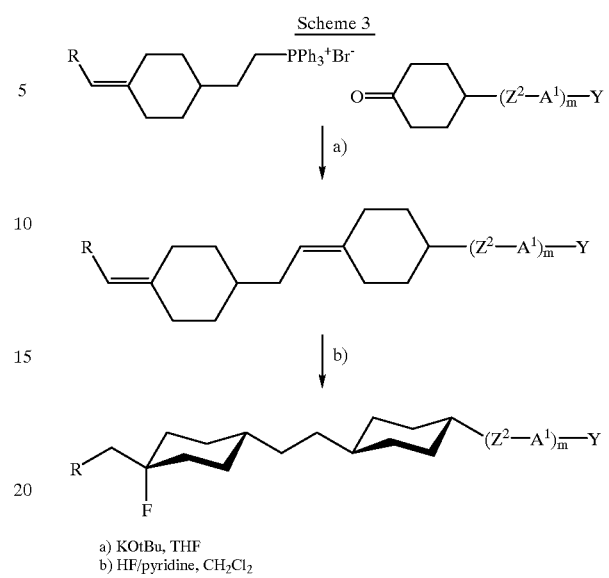
a) KOtBu, THF
b) HF/pyridine, CH$_2$Cl$_2$
a) R CH$_2$PPh$_3$+Br-, KOtBu, THF
b) Ethylene glycol, cat. TsOH, toluene
c) LiAlH$_4$ THF
d) PPh$_3$, CBr$_4$, CH$_3$CN
e) PPh$_3$, DMPU
f) HCOOH, toluene
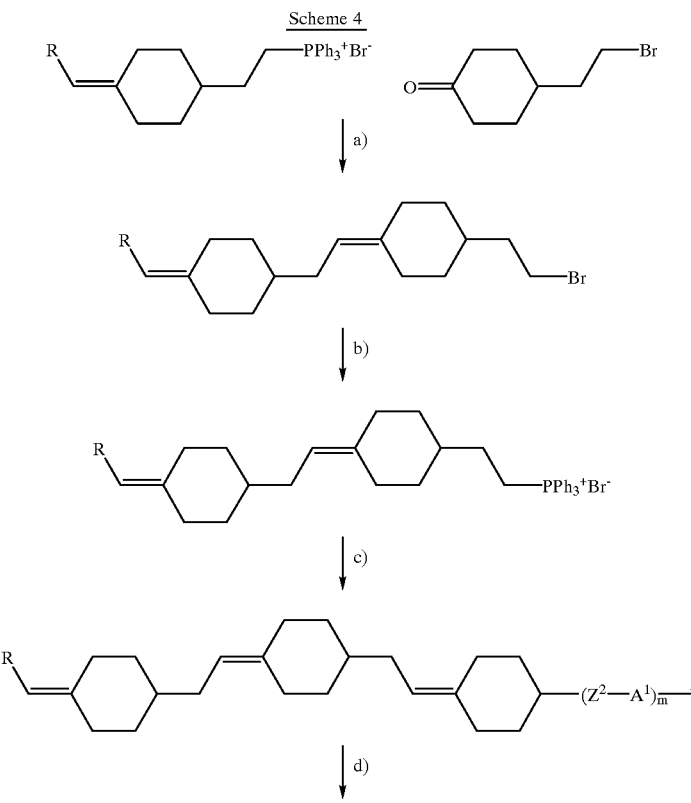

-continued
a) KOtBu, THF
b) PPh₃, DMPU
c) 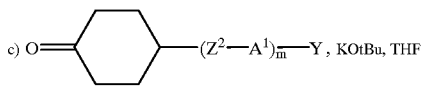, KOtBu, THF
d) HF/pyridine, CH₂Cl₂
Scheme 5
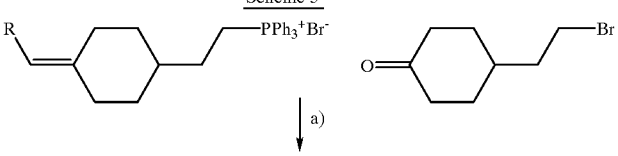
↓ a)
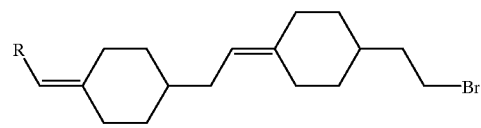
↓ b)
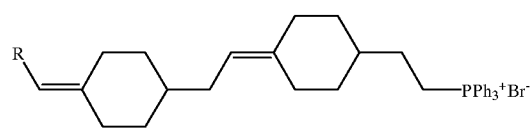
↓ c)
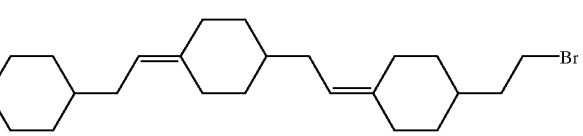
↓ b)
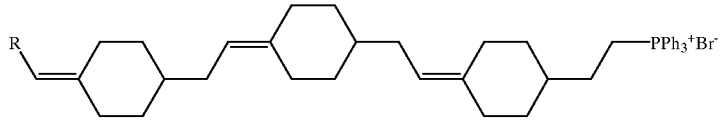
↓ d)
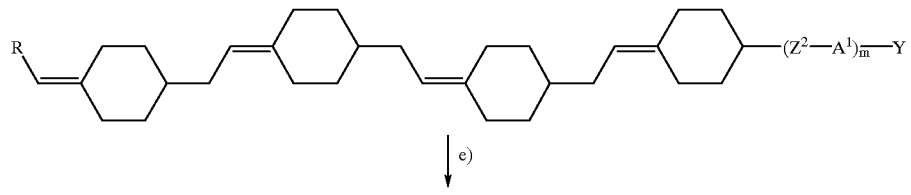
↓ e)

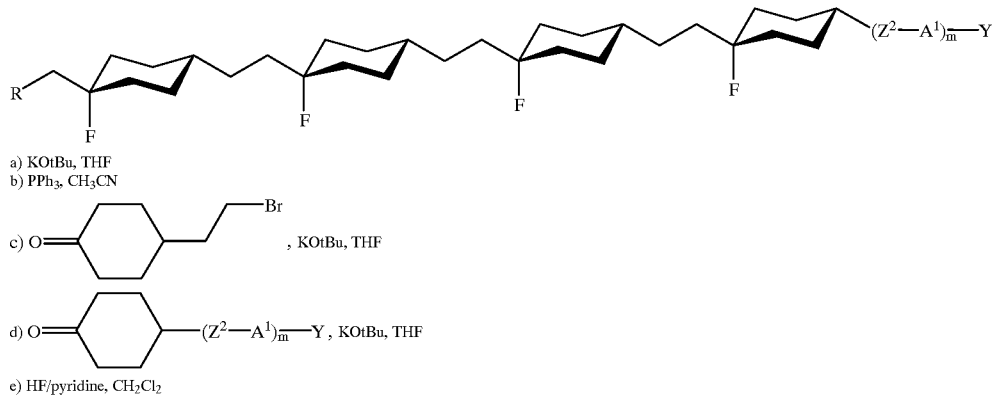
a) KOtBu, THF
b) PPh$_3$, CH$_3$CN
c) 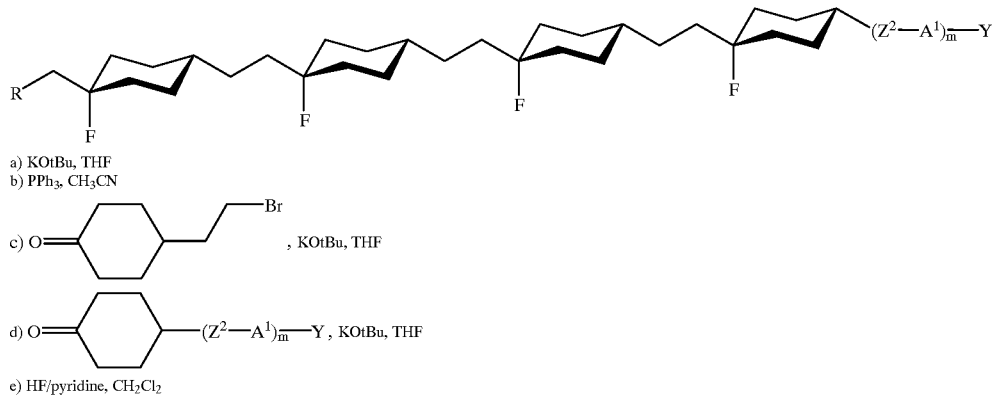, KOtBu, THF
d) 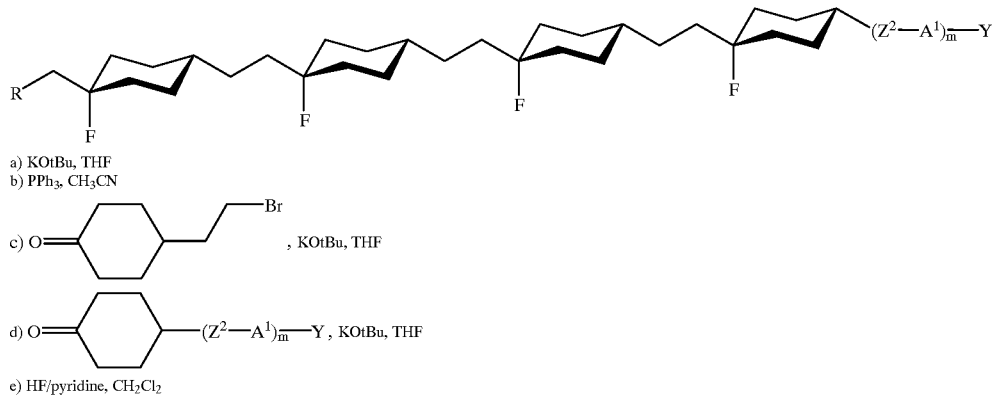, KOtBu, THF
e) HF/pyridine, CH$_2$Cl$_2$
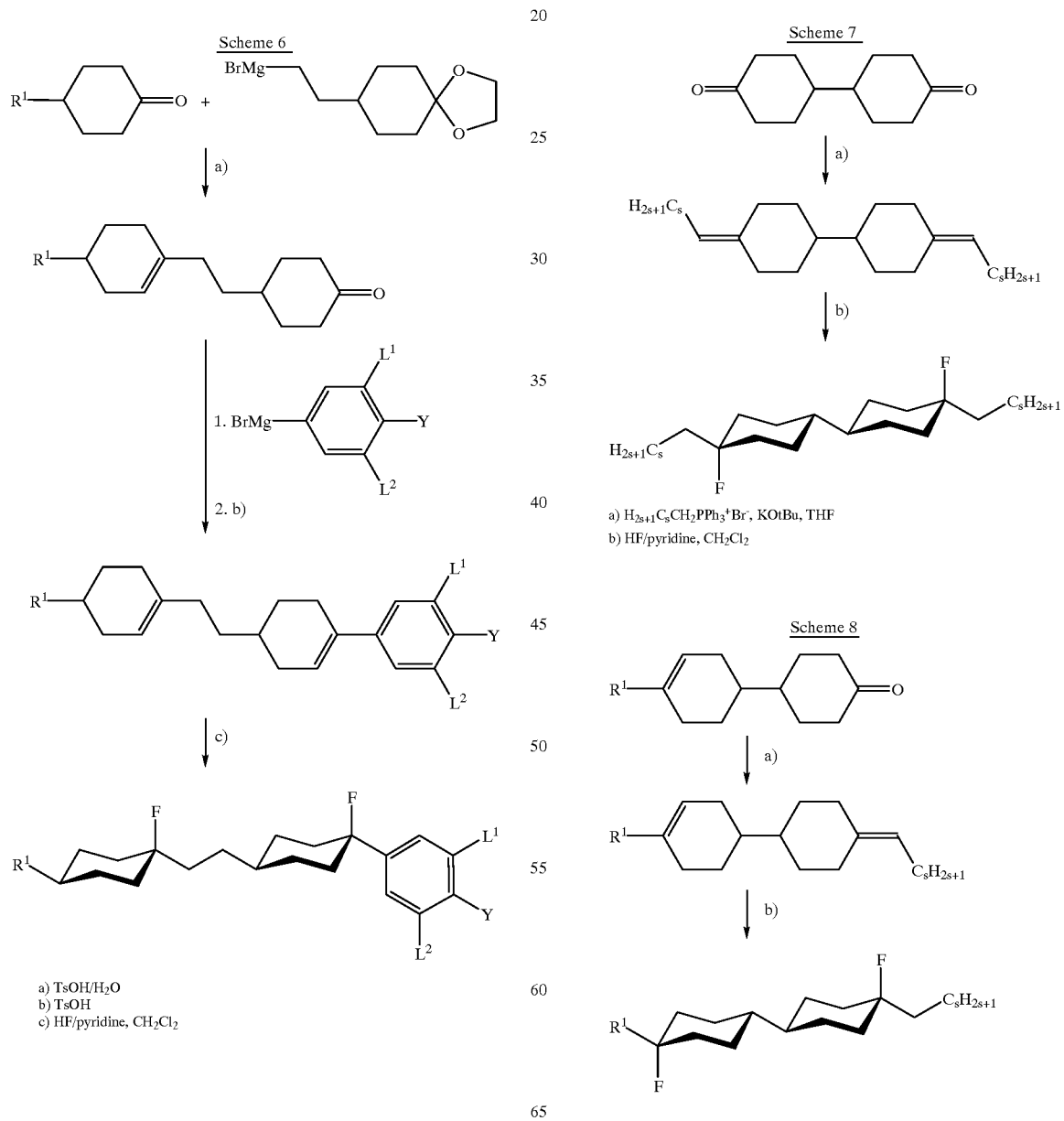

-continued a) H$_{2s+1}$C$_s$CH$_2$PPh$_3$$^+$Br$^-$, KOtBu, THF
b) HF/pyridine, CH$_2$Cl$_2$ Esters of the formula I can also be obtained by esterification of corresponding carboxylic acids (or reactive derivatives thereof) using alcohols or phenols (or reactive derivatives thereof) or by the DCC method (DCC =dicyclohexylcarbodiimide).

The corresponding carboxylic acids and alcohols or phenols are known or can be prepared analogously to known processes.

In a further process for the preparation of compounds of the formula I in which Z$^1$ or Z$^2$ is —CH═CH—, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines which are necessary for the success of the coupling reaction, such as, for example, triethylamine, are also suitable as solvent.

Examples of suitable palladium catalysts are palladium salts, in particular Pd(II) acetate, and organophosphorous (III) compounds, such as, for example, triarylphosphines. Reaction can be carried out in the presence or absence of an inert solvent, at temperatures between 0° C. and 150° C., preferably between 20° C. and 100° C.; examples of suitable solvents are nitriles, such as acetonitrile, or hydrocarbons, such as benzene or toluene. The aryl halides and olefins employed as starting materials are frequently commercially available or can be prepared by processes known from the literature, for example by halogenation of corresponding parent compounds or by elimination reactions on corresponding alcohols or halides.

In this way, for example, stilbene derivatives can be prepared. Stilbenes can furthermore be prepared by reacting a 4-substituted benzaldehyde with a corresponding phosphorous ylide by the Wittig method. However, it is also possible to prepare tolans of the formula I by using mono-substituted acetylene instead of the olefin (Synthesis 627 (1980) or Tetrahedron Lett. 27, 1171 (1986)).

Furthermore, the coupling of aromatic compounds can be carried out by reacting aryl halides with aryltin compounds. These reactions are preferably carried out with addition of a catalyst, such as, for example, a palladium(0) complex, in inert solvents, such as hydrocarbons, at high temperatures, for example in boiling xylene under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I in which Z$^1$ or Z$^2$ is —C≡C— can also be prepared by Fritsch-Buttenberg-Wiechell rearrangement (Ann. 279, 319, 1984), in which 1,1-diaryl-2-haloethylenes are rearranged in the presence of strong bases to give diarylacetylenes.

Tolans of the formula I can also be prepared by brominating the corresponding stilbenes, and then subjecting the products to dehydrohalogenation. Use can also be made here of variants of this reaction which are known per se, but are not mentioned here in greater detail.

Ethers of the formula I are obtainable by esterification of corresponding hydroxyl compounds, preferably corresponding phenols, where the hydroxyl compound is advantageously first converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This alkoxide or phenoxide can then be reacted with the appropriate alkyl halide, alkyl sulphonate or dialkyl sulphate, advantageously in an inert solvent, such as, for example, acetone, 1,2-dimethoxyethane, DMF or dimethyl sulphoxide, or alternatively with an excess of aqueous or aqueous-alcoholic NaOH or KOH, at temperatures between about 20° C. and 100° C.

The starting materials are either known or can be prepared analogously to known compounds.

The liquid-crystalline media according to the invention preferably comprise from 2 to 40, in particular from 4 to 30, components as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyl-dioxanes, phenyl- or cyclohexyl-1,3-dithianes, 1,2-di-phenylethanes, 1,2-dicyclohexylethanes, 1-phenyl-2-cyclohexylethanes, 1-cyclohexyl-2-(4-phenylcyclohexyl)-ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4 -cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labeled with the subformulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+l)}$F$_k$Cl$_l$, where i is 0 or 1, and k and l are 1, 2 or 3; the compounds in which R" has this meaning are labeled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the subformulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is known as group C below, and the compounds of this subgroup are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably Group A: from 0 to 90%, preferably from 20 to 90%, in particular from 30 to 90%

Group B: from 0 to 80%, preferably from 10 to 80%, in particular from 10 to 65%

Group C: from 0 to 80%, preferably from 5 to 80%, in particular from 5 to 50%, the sum of the proportions by weight of the group A and/or B and/or C compounds present in the particular media according to the invention preferably being 5%–90% and in particular from 0% to 90%.

The media according to the invention preferably comprise from 1 to 40%, particularly preferably from 5 to 30%, of compounds according to the invention. Further preferred media are those which comprise more than 40%, in particular from 45 to 90%, of compounds according to the invention. The media preferably comprise three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 197 14 231.1, filed Apr. 7, 1997 is hereby incorporated by reference.

EXAMPLES

The examples below are intended to illustrate the invention without representing a limitation. Above and below, percent data are percent by weight. All temperatures are given in degrees Celsius. m.p.=melting point, cl.p.=clearing point. Furthermore, C=crystalline state, N=nematic phase, S=smectic phase and I=isotropic phase. The number between two symbols indicates the conversion temperature in degrees Celsius. Δn denotes optical anisotropy (589 nm, 20° C.). The viscosity (mm$^2$/sec) was determined at 20° C.

"Conventional work-up" means that water is added if necessary, the mixture is extracted with methylene chloride, diethyl ether, or toluene, the organic phase is separated off, dried and evaporated, and the product is purified by distillation under reduced pressure or crystallization and/or chromatography.

The following abbreviations are used:

THF tetrahydrofuran
KOtBu potassium tert-butoxide
RT room temperature

Example 1

29.1 g of bicyclohexyl-4,4'-dione and 123 g of propyltriphenylphosphonium bromide were suspended in 300 ml of THF. The solution was cooled to 0° C., and a solution of 36 g of potassium tert-butoxide in 100 ml of THF was added dropwise, and the mixture was stirred at RT overnight. Conventional work-up gave 4,4'-dipropylidenebicyclohexyl.

Example 2

25 g of 4,4'-dipropylidenebicyclohexyl were dissolved in 50 ml of dichloromethane, and the solution was added dropwise, with stirring, to a 70% solution, cooled to −20° C., of hydrogen fluoride in pyridine. The mixture was stirred at RT overnight and worked up as in Example 35, giving 4,4'-difluoro-4,4'-dipropylbicyclohexyl.

The following compounds according to the invention are obtained analogously from the corresponding precursors:

Examples 3–16

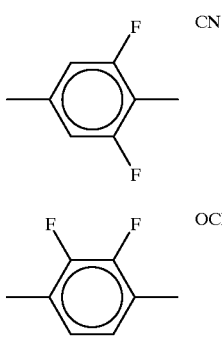

| n | R¹ | Y | | |
|---|---|---|---|---|
| (3) | 1 | ethyl | ethyl | |
| (4) | 1 | n-butyl | n-butyl | |
| (5) | 1 | n-pentyl | n-pentyl | Δε −2.5, Δn 0.040 |
| (6) | 1 | n-hexyl | n-hexyl | |
| (7) | 1 | ethyl | n-propyl | |
| (8) | 1 | n-propyl | n-butyl | |
| (9) | 1 | n-propyl | n-pentyl | C 142 I |
| | | | | Δε −2.5. Δn 0.043 |
| (10) | 1 | n-butyl | n-pentyl | |
| (11) | 1 | n-pentyl | CH=CH$_2$ | |
| (12) | 1 | n-propyl | trans-(CH$_2$)$_2$CH=CHCH$_3$ | |
| (13) | 1 | CH=CH$_2$ | CH=CH$_2$ | |
| (14) | 2 | n-propyl | n-propyl | |
| (15) | 2 | n-pentyl | n-pentyl | |
| (16) | 2 | n-propyl | n-pentyl | |

Examples 17–22

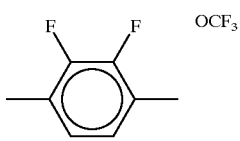

| | R¹ | Z² | A¹ | Y |
|---|---|---|---|---|
| (17) | n-propyl | — | 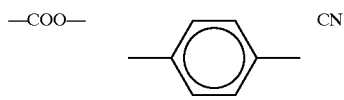 | F |
| (18) | n-pentyl | — | (tetrafluoro phenyl) | CN |
| (19) | n-propyl | — | (difluoro phenyl) | OCF$_3$ |
| (20) | n-pentyl | —COO— | (phenyl) | CN |
| (21) | n-pentyl | —CH=CH— | 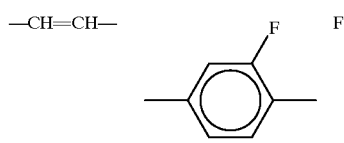 | F |

-continued

| | R¹ | Z² | A¹ | Y |
|---|---|---|---|---|
| (22) | n-propyl | — | (phenyl) | O-n-propyl |

Examples 23–29

| | n | R¹ | Y |
|---|---|---|---|
| (23) | 1 | ethyl | ethyl |
| (24) | 1 | n-pentyl | n-propyl |
| (25) | 1 | n-pentyl | n-pentyl |
| (26) | 1 | n-propyl | n-pentyl |
| (27) | 2 | n-propyl | n-propyl |
| (28) | 2 | n-pentyl | n-pentyl |
| (29) | 2 | n-pentyl | n-propyl |

Example 30

64.4 g of methyl (4-oxocyclohexyl)acetate and 137.9 g of propyltriphenylphosphonium bromide were introduced into 500 ml of THF, and the mixture was cooled to −10° C. with stirring under nitrogen. A solution of 40.17 g of potassium tert-butoxide in 400 ml of THF was then added dropwise with stirring at the same temperature, and the mixture was then stirred at RT for a further 2 h. Conventional work-up gave methyl (4-propylidenecyclohexyl)acetate.

Example 31

25.2 g of lithium aluminium hydride were introduced into 100 ml of THF, and a solution of 54.2 g of methyl (4-propylidenecyclohexyl)acetate in 200 ml of THF was then added dropwise with stirring at such a rate that the reaction boiled gently. The mixture was then refluxed for a further 3 h, cooled to RT and hydrolysed dropwise with 50 ml of water. 18% hydrochloric acid was then added until the precipitate formed had dissolved. Conventional work-up gave 2-(4-propylidenecyclohexyl)ethanol (boiling point 110° C. at 10 mmHg).

Example 32

40.4 g of 2-(4-propylidenecyclohexyl)ethanol, 69.5 g of triphenylphosphine and 500 ml of acetonitrile were cooled to −5° C. A solution of 99.5 g of tetrabromomethane in 100 ml of acetonitrile was then added with stirring, and the mixture was stirred at RT overnight. The solvent was then removed, and the residue was subjected to conventional work-up, giving 1-(2-bromo-ethyl)-4-propylidenecyclohexane.

Example 33

43.7 g of 1-(2-bromomethyl)-4-propylidenecyclohexane, 45.9 g of triphenylphosphine and 0.5 ml of triethylamine were dissolved in 110 ml of 1,3-dimethyl-tetrahydropyrimidone, and the mixture was stirred overnight at 75° C. under a nitrogen atmosphere. Conventional work-up gave triphenyl[2-(4-propylidenecyclohexyl)ethyl]phosphonium bromide.

Example 34

57.0 g of 4-propylcyclohexanone and 25.0 g of triphenyl[2-(4-propylidenecyclohexyl)ethyl]phosphonium bromide were introduced into 150 ml of THF under nitrogen, and the mixture was cooled to −10° C. A solution of 5.61 g of potassium tert-butoxide in 100 ml of THF was then added dropwise with stirring, and the mixture was stirred at RT for a further 2 h. Conventional work-up gave 4-[2-(4-propylcyclohexylidene)ethyl]propylidenecyclohexane.

Example 35

68.0 g of 4-[2-(4-propylcyclohexylidene)ethyl]-propylidenecyclohexane were dissolved in 30 ml of dichloromethane and added dropwise to a 70% solution, cooled to −15° C., of hydrogen fluoride in pyridine. The mixture was stirred at 10° C. for 10 minutes, and the reaction batch was poured into a mixture of 300 g of ice and 50 g of sodium hydrogencarbonate. After extraction with hexane and removal of the solvent, the residue was prepurified by means of a short silica-gel frit (eluent petroleum ether/ethyl acetate 1/1), and the eluate was evaporated to give a residue. The residue was crystallized from hexane, giving 1-fluoro-4-[2-(1-fluoro-4-propylcyclohexyl)ethyl]propylcyclohexane ($C_{78}$ SmB 104 I, $\Delta\epsilon$ −4.6, $\Delta n$ 0.048).

The following compounds according to the invention are obtained analogously from the corresponding precursors:

Examples 36–51

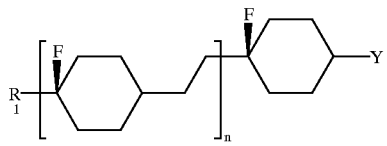

| | n | $R^1$ | Y | |
|---|---|---|---|---|
| (36) | 1 | ethyl | ethyl | |
| (37) | 1 | n-butyl | n-butyl | |
| (38) | 1 | n-pentyl | n-pentyl | C 70 SmB 138 I |
| | | | | $\Delta\epsilon$ −3.8, $\Delta n$ 0.036 |
| (39) | 1 | n-hexyl | n-hexyl | |
| (40) | 1 | ethyl | n-propyl | |
| (41) | 1 | n-propyl | n-butyl | |
| (42) | 1 | n-propyl | n-pentyl | C 68 SmB 120 I |
| | | | | $\Delta\epsilon$ −4.1, $\Delta n$ 0.050 |
| (43) | 1 | n-butyl | n-pentyl | |
| (44) | 1 | n-heptyl | n-pentyl | Mp 73, |
| | | | | $\Delta\epsilon$ −3.5, $\Delta n$ 0.024 |
| (45) | 1 | n-pentyl | $CH=CH_2$ | |
| (46) | 1 | n-propyl | trans-$(CH_2)_2CH=CHCH_3$ | |
| (47) | 1 | $CH=CH_2$ | $CH=CH_2$ | |
| (48) | 2 | n-propyl | n-propyl | |
| (49) | 2 | n-pentyl | n-pentyl | |
| (50) | 2 | n-propyl | n-pentyl | |
| (51) | 2 | n-propyl | ethyl | |
| (52) | 1 | n-propyl | ethyl | Mp 87, |
| | | | | $\Delta\epsilon$ −3.5, $\Delta n$ 0.033 |
| (53) | 1 | $(CH_2)_2CH=CH$ | $CH=CH_2$ | K 74 SmB (70) N 83 I |
| | | | | $\Delta\epsilon$ −3.6, $\Delta n$ 0.051 |

Examples 54–62

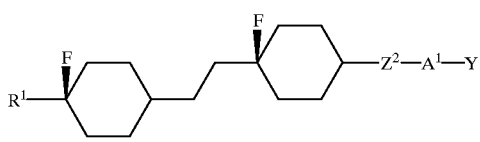

| | $R^1$ | $Z^2$ | $A^1$ | Y |
|---|---|---|---|---|
| (54) | n-propyl | — | 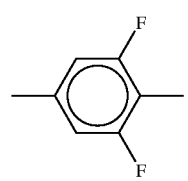 | |

-continued
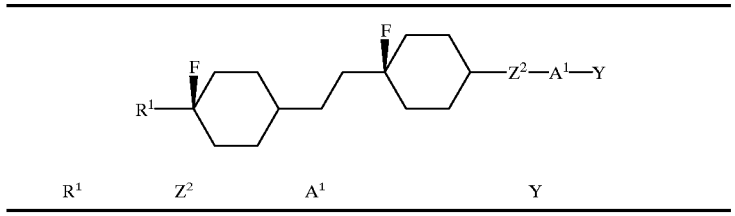
| | R$^1$ | Z$^2$ | A$^1$ | Y | |
|---|---|---|---|---|---|
| (55) | n-pentyl | — | (F,F,F-phenyl) | CN | |
| (56) | n-propyl | — | (F,F-phenyl) | OCF$_3$ | |
| (57) | n-pentyl | —COO— | (phenyl) | CN | |
| (58) | n-pentyl | —CH=CH— | (F-phenyl) | F | |
| (59) | n-propyl | — | (phenyl) | O-n-propyl | |
| (60) | n-propyl | — | | ethyl | |
| (61) | n-propyl | — | | n-propyl | Mp 100 |
| (62) | n-propyl | — | | n-pentyl | |
Examples 63–65
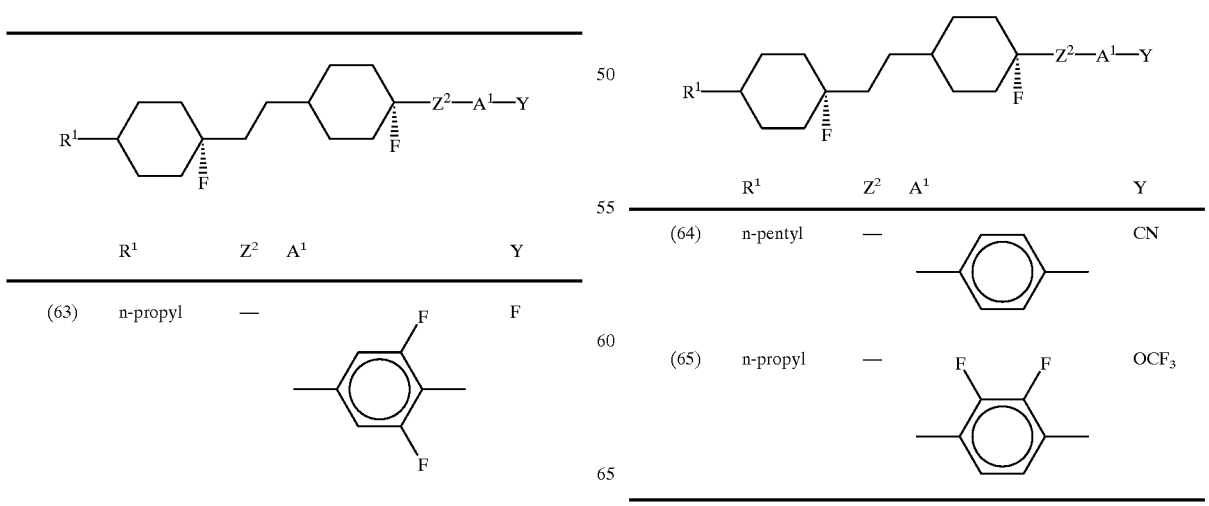
| | R$^1$ | Z$^2$ | A$^1$ | Y |
|---|---|---|---|---|
| (63) | n-propyl | — | (F,F,F-phenyl) | F |
| (64) | n-pentyl | — | (phenyl) | CN |
| (65) | n-propyl | — | (F,F-phenyl) | OCF$_3$ |

Examples 66–72

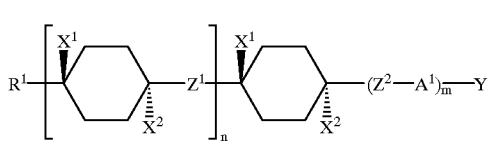

| | n | R¹ | Y |
|---|---|---|---|
| (66) | 1 | ethyl | ethyl |
| (67) | 1 | n-pentyl | n-propyl |
| (68) | 1 | n-pentyl | n-pentyl |
| (69) | 1 | n-propyl | n-pentyl |
| (70) | 2 | n-propyl | n-propyl |
| (71) | 2 | n-pentyl | n-pentyl |
| (72) | 2 | n-pentyl | n-propyl |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A fluorocyclohexane compound of the formula I

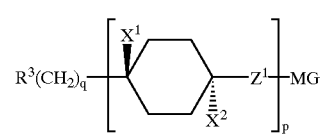

in which

Y is alkyl or alkoxy having 1 to 10 carbon atoms which is unsubstituted or at least monosubstituted by halogen, alkenyl or alkenyloxy having 2 to 10 carbon atoms which is unsubstituted or at least monosubstituted by —CN, —CF₃, or —F, or Y is —CN, —F, —CF₃, —OCHF₂, —OCF₃, —OCHFCF₃ or —OCF₂CF₃.

$X_1$ and $X_2$ are each, independently of one another, H or F in the axial position, where $X^1$ and $X^2$ are not simultaneously H on each individual cyclohexane ring substituted by $X^1$ and $X^2$, R¹ is H, an alkyl or alkenyl radical having 1–12 or 2–12 carbon atoms respectively which is unsubstituted, monosubstituted by CN or CF₃ or at least monosubstituted by halogen, where one or more CH₂ groups in these radicals, in each case independently of one another, are optionally replaced by —O—, —S—, —CO—,

—CO—O—, —O—CO— or —O—CO—O— in such a way that the heteroatoms are not linked directly to one another, A¹ a) is a trans-1,4-cyclohexylene radical, in which, in addition, one or more non-adjacent CH₂ groups are optionally replaced by —O— and/or —S—, b) is a 1,4-phenylene radical, in which, in addition, one or two CH groups are optionally replaced by N, c) is a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl, d) is 1,4-cyclohexenylene, where the radicals a), b) and d) are optionally substituted by CN, Cl or F, $Z^1$ and $Z^2$ are each, independently of one another, —CO—O—, —O—CO—, —CH₂O—, —O—, —O—CH₂—, —CH₂CH₂—, —CH=CH—, —C≡C— or a single bond, n is 1, 2, 3 or 4, and m is 0, 1 or 2, where m+n is 1, 2, 3 or 4.

2. A compound of claim 1, wherein $X^1$ and $X^2$ are not simultaneously F on each individual cyclohexane ring substituted by $X^1$ and $X^2$.

3. A compound of claim 1, wherein $Z^1$ is —CH₂CH₂—, —CH=CH— or a single bond.

4. A compound of claim 1, wherein R¹ is straight-chain alkyl or alkoxy radical having 1 to 10 carbon atoms or alkenyl radical having 2 to 10 carbon atoms, and Y is alkyl having 1 to 10 carbon atoms, alkenyl having 2 to 10 carbon atoms, —CN, —F, —OCHF₂ or —OCF₃.

5. A compound of claim 1, wherein the radicals R¹ and Y are simultaneously alkyl having 1 to 10 carbon atoms, and m is 0.

6. A liquid-crystalline medium having at least two liquid-crystalline components, which comprises at least one compound of the formula I of claim 1.

7. A liquid-crystal display element, which comprises a liquid-crystalline medium according to claim 6.

8. An electro-optical display element, which comprises as dielectric, a liquid crystalline medium according to claim 6.

9. A fluorocyclohexane compound of claim 1, which has a highly negative dielectric anisotropy, Δε, of –2.5 or less.

10. A fluorocyclohexane compound of claim 1, which has a low optical anisotropy, Δn, of 0.051 or less.

11. A fluorocyclohexane compound of claim 1, which has a highly negative dielectric anisotropy, Δε, of –2.5 or less and a low optical anisotropy, Δn, of 0.051 or less.

12. A process for the preparation of an axially fluorinated cyclohexane of the formula II

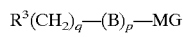

comprising adducting hydrogen fluoride onto an unsaturated starting compound of the formula III R³(CH₂)q—(B)p—MG    III in which B is

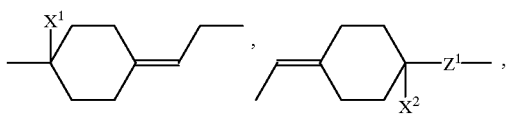

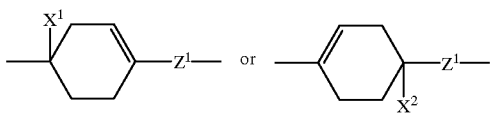

$R^3$ is H, an alkyl or alkenyl radical having 1–12 carbon atoms, which is unsubstituted, monosubstituted by CN or $CF_3$ or at least monosubstituted by halogen, where one or more $CH_2$ groups in these radicals, in each case independently of one another, are optionally replaced by —O—, —S—, —CO—,

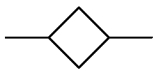

—CO—O—, —O—CO— or —O—CO—O— in such a way that heteroatoms are not linked directly to one another, p is 1,2,3,4 or 5, q is 0 or 1, MG is a mesogenic group, $X_1$ and $X_2$ are each, independently of one another, H or F in the axial position, where $X^1$ and $X^2$ are not simultaneously H on each individual cyclohexane ring substituted by $X^1$ and $X^2$, and $Z^1$ is —CO—O—, —O—CO—, —$CH_2$O—, —O—, —O—$CH_2$, —$CH_2CH_2$—, —CH=CH—, —C≡C— or a single bond.

13. The process of claim 12, wherein the adducting of hydrogen fluoride onto the compound of formula III is conducted at a temperature of −78° C. to +50° C.

14. The process of claim 12, wherein the adducting of hydrogen fluoride onto the compound of formula III is conducted in the presence of a halogenated hydrocarbon or ether solvent.

15. The process of claim 12, wherein the hydrogen fluoride is provided in the form of an amine adduct.

16. The process of claim 15, wherein the hydrogen fluoride is adducted with pyridine, a polyvinyl pyridine or a trialkylamine.

17. The process of claim 15, wherein the hydrogen fluoride is provided in solution with pyridine wherein the proportion by weight of hydrogen fluoride is 70% based on the solution.

18. The process of claim 12, wherein the compound of formula III and the hydrogen fluoride are provided in a molar ratio of from 1.0 to 10.

19. The process of claim 12, wherein in formulae II and III, MG is of the following formula:

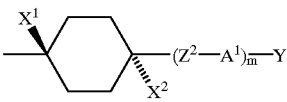

wherein $X^1$ and $X^2$ are as defined, $Z^2$ independently has the meaning given for $Z^1$, $A^1$ a) is a trans-1,4-cyclohexylene radical, in which, in addition, one or more non-adjacent $CH_2$ groups are optionally replaced by —O— and/or —S—, b) is a 1,4-phenylene radical, in which, in addition, one or two CH groups are optionally replaced by N, c) is a radical from the group consisting of 1,4-bicyclo[2.2.2]piperidine-1,4-diyl, naphthalene-2,6-diyl, decahydronaphthalene-2,6-diyl and 1,2,3,4-tetrahydronaphthalene-2,6-diyl, d) is 1,4-cyclohexenylene, where the radicals a), b) and d) are optionally substituted by CN, Cl or F, Y is alkyl or alkoxy having 1 to 10 carbon atoms which is unsubstituted or at least monosubstituted by halogen, alkenyl or alkenyloxy having 2 to 10 carbon atoms which is unsubstituted or at least monosubstituted by —CN, $CF_3$, or —F, or Y is —CN, —F, —$CF_3$, —$OCHF_2$, —$OCF_3$, —$OCHFCF_3$ or —$OCF_2CF_3$, and m is 0, 1 or 2.

* * * * *